(12) United States Patent
Hussain

(10) Patent No.: US 7,999,134 B2
(45) Date of Patent: Aug. 16, 2011

(54) CRYSTALLIZATION OF IODIXANOL USING MILLING

(75) Inventor: Khalid Hussain, Oslo (NO)

(73) Assignee: GE Healthcare AS, Oslo (NO)

( * ) Notice: Subject to any disclaimer, the term of this patent is extended or adjusted under 35 U.S.C. 154(b) by 0 days.

(21) Appl. No.: 12/611,956

(22) Filed: Nov. 4, 2009

(65) Prior Publication Data

US 2011/0021826 A1    Jan. 27, 2011

Related U.S. Application Data

(60) Provisional application No. 61/227,106, filed on Jul. 21, 2009.

(51) Int. Cl.
*C07C 233/65* (2006.01)
(52) U.S. Cl. .................. 564/153; 424/9.452; 216/52
(58) Field of Classification Search ............... 564/153; 424/9.452; 216/52
See application file for complete search history.

(56) References Cited

U.S. PATENT DOCUMENTS

| 5,525,328 A | 6/1996 | Bacon et al. |
| 2008/0287711 A1 | 11/2008 | Strandmyr |

*Primary Examiner* — Shailendra Kumar

(57) ABSTRACT

This invention relates to the manufacture of iodixanol(1,3-bis (acetamido)-N,N'-bis[3,5-bis(2,3-dihydroxypropylaminocarbonyl)-2,4,6-triiodophenyl]-2-hydroxypropane), more specifically to the purification of iodixanol by crystallization by using wet milling.

1 Claim, 2 Drawing Sheets

Iodixanol agglomerates produced according to Example 1.
Scale: 1 unit = 120 μm.

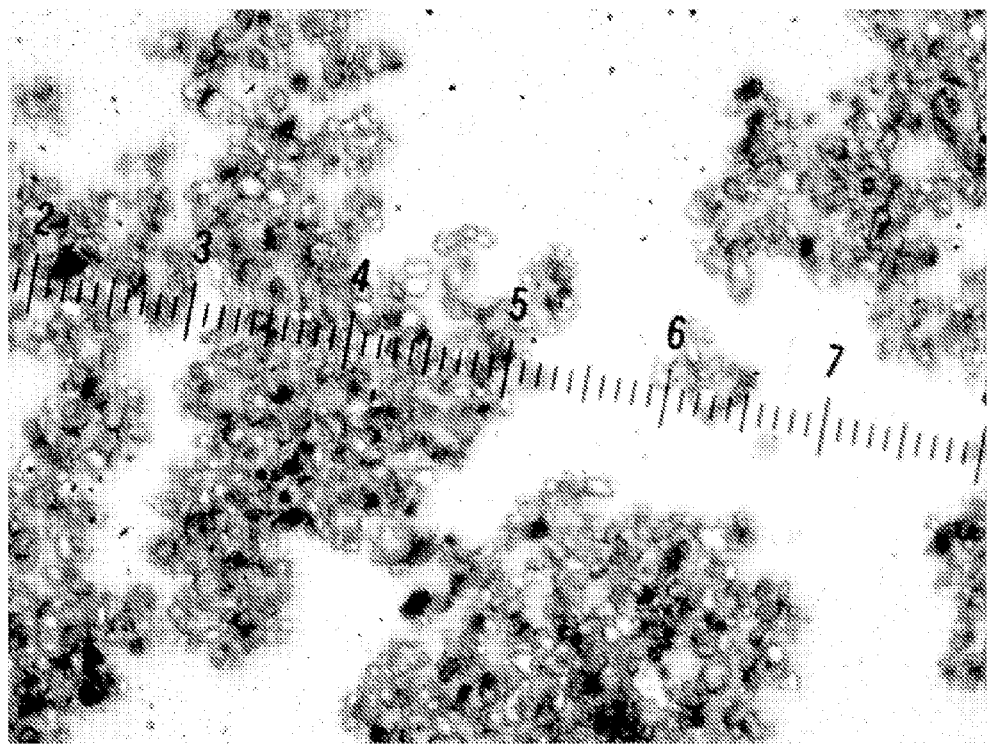
Iodixanol particles produced according to Example 2.
Scale: 1 unit = 30 μm.
FIG.2
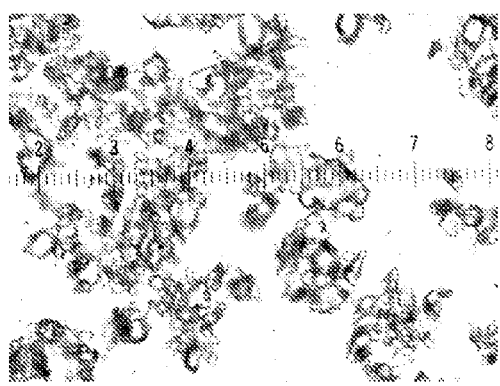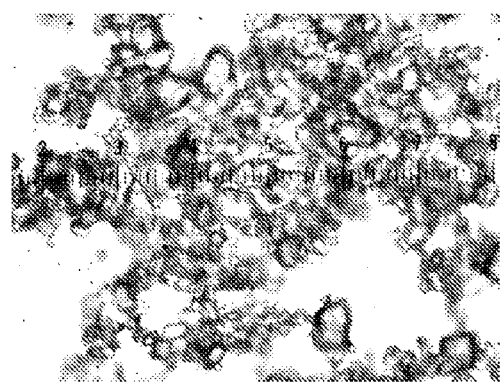
Iodixanol particles produced according to Example 4. Scale: 1 unit = 30 μm.
FIG.3A
Iodixanol particles produced according to Example 4. Scale: 1 unit = 30 μm.
FIG.3B

CRYSTALLIZATION OF IODIXANOL USING MILLING

CROSS REFERENCE TO RELATED APPLICATIONS

The present application claims benefit of priority under 35 U.S.C. §119(e) to U.S. Provisional Application No. 61/227,106 filed Jul. 21, 2009, the entire disclosure of which is hereby incorporated by reference.

TECHNICAL FIELD

This invention relates to the manufacture of iodixanol(1,3-bis(acetamido)-N,N'-bis[3,5-bis(2,3-dihydroxypropylaminocarbonyl)-2,4,6-triiodophenyl]-2-hydroxypropane), more specifically to the purification of iodixanol by crystallization.

BACKGROUND OF THE INVENTION

Iodixanol is the non-proprietory name of the chemical drug substance of a non-ionic X-ray contrast agent marketed under the trade name Visipaque™. Visipaque™ is one of the most used agents in diagnostic X-ray procedures and is manufactured in large quantities.

The manufacture of such non-ionic X-ray contrast agents involves the production of the chemical drug substance (referred to as primary production) followed by formulation into the drug product (referred to as secondary production). Primary production of iodixanol involves a multi step chemical synthesis and a thorough purification process. For a commercial drug product it is important for the primary production to be efficient and economical and to provide a drug substance fulfilling the specifications, e.g. as expressed in the US Pharmacopeia.

A number of methods are known for the preparation of iodixanol. These are all multi step chemical synthetic processes and the cost of the final formulated product thus mainly depends on these processes. It is therefore important to optimize the processes both for economic and environmental reasons.

Three main chemical synthetic processes are known for the preparation of iodixanol, all of which start with 5-nitroisophthalic acid. In the first process described in EP 108638, which document is hereby incorporated by reference, the final intermediate 5-acetamido-N,N'-bis(2,3-dihydroxypropyl)-2,4,6-triiodo-isophthalamide (hereinafter "Compound A") is reacted with a dimerisation agent such as epichlorohydrin to yield the drug substance, see Scheme I.

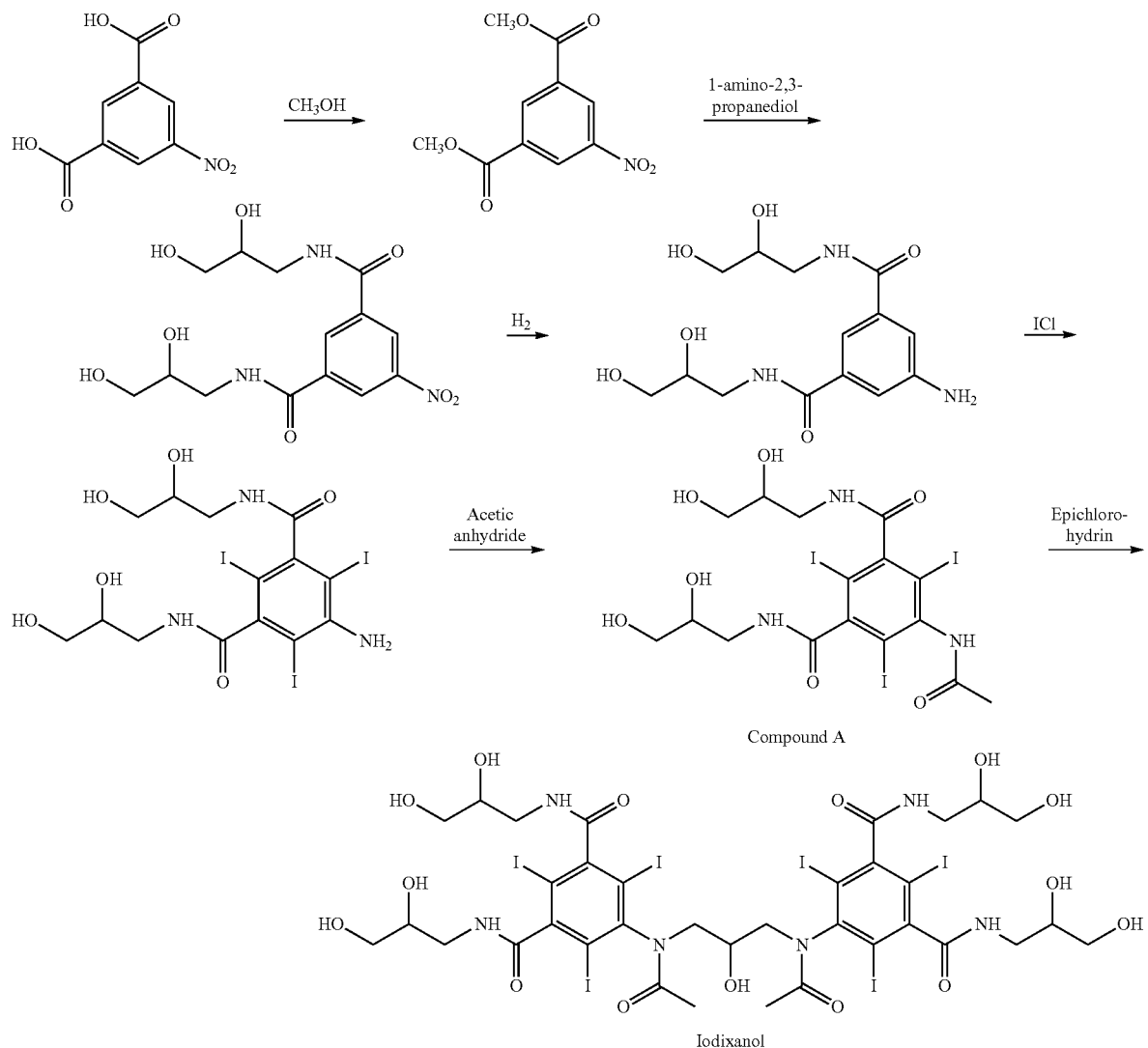

Scheme I

The overall yield in this process is relatively low and the purification of the end product iodixanol is expensive and time consuming. The purification process described in EP patent 108638 involves purification by preparative liquid chromatography. The use of preparative liquid chromatography is a serious disadvantage in industrial processes in particular due to the high costs involved.

Several attempts have been made to find alternative manufacturing processes. Attempts to increase the yield of the chemical synthesis is published by Priebe et. al. (Acta Radiol. 36 (1995), Suppl. 399, 21-31). This publication describes another route which avoids the difficult last step of the process of Scheme I. However, the route involves eight reaction steps from 5-nitroisophthalic acid, which is undesirable, and one of the steps includes chlorination with thionyl chloride, which is extremely corrosive. Also, the introduction of the iodine atoms takes place very early in the sequence, which is disadvantageous as iodine is the most expensive reagent in the process. The yield and final purification method for this route have not been reported.

The third route to iodixanol involves the synthesis of 5-amino-2,4,6-triiodoisophthalic acid (WO 96/37458) and then its dichloride (WO 96/37459), followed by conversion into Compound A (U.S. Pat. No. 5,705,692) and finally dimerisation as in the process of Scheme I. This method thus has the same disadvantages as the first process, and also uses an undesirable acid chlorination step.

A common system for purification of the crude product in the final step of the primary production process, avoiding the liquid chromatography method, has been purification by crystallization. To achieve the desired purity, the crude iodixanol produced by the synthetic chemical process is crystallized twice. The process is time consuming and takes about 3 days for the first crystallization and about 2 days for the second one. Hence, the crystallization process is very demanding in terms of time and equipment size, it will take several days to perform and is often a bottleneck in industrial scale processes.

WO 99/18054 describes a process for the crystallization of i.a. iodixanol where the crystallization is effected with high thermal energy, specifically under elevated pressure and at a temperature above the boiling point of the solution at atmospheric pressure.

WO 00/47549 describes a process for the preparation of iodixanol where unreacted Compound A is precipitated from the reaction mixture and recovered for reuse in a later batch.

It is hence a desire to shorten the crystallization time and also improve the crystallization step in order to increase the purity of the final product.

BRIEF DESCRIPTION OF THE DRAWINGS

FIG. 2 shows iodixanol particles produced in a crystallization step according to the present invention. Scale: 1 unit=30 μm.

FIGS. 3A and 3B show iodixanol particles produced in a crystallization step according to the present invention. Scale: 1 unit=30 μm.

SUMMARY OF THE INVENTION

Figure 1:
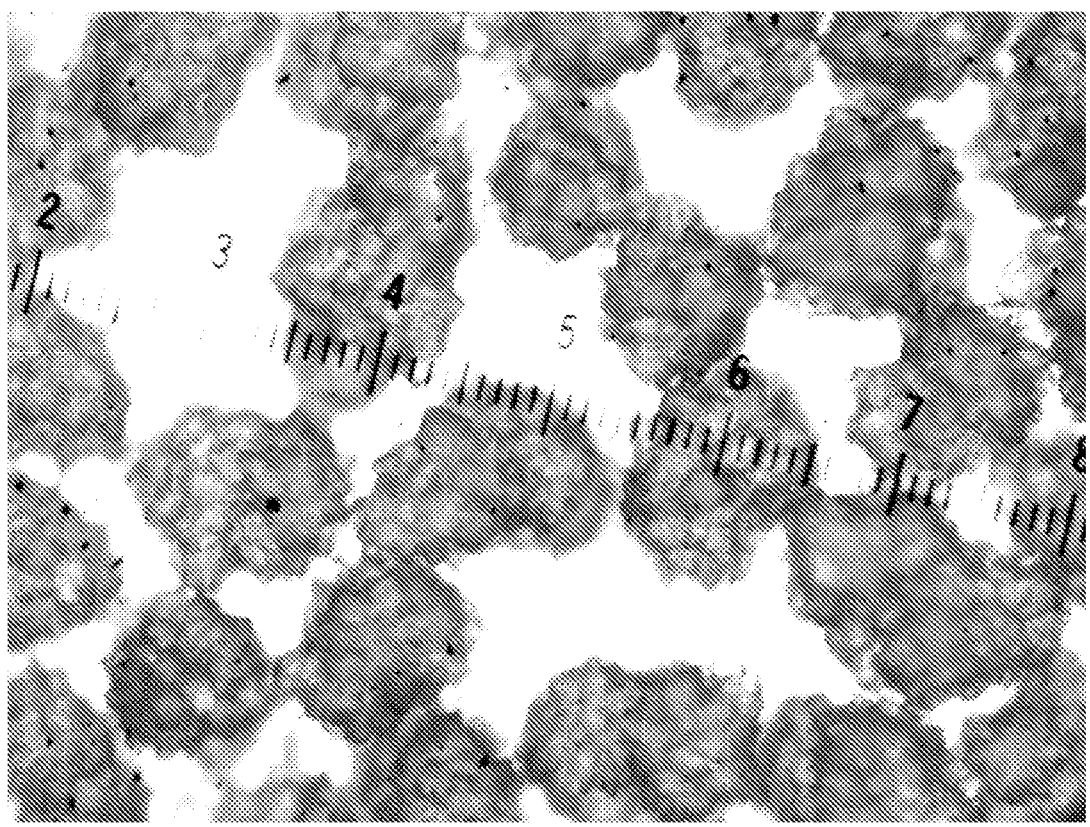
FIG. 1 shows agglomerates of iodixanol produced in a crystallization step according to prior art. Scale: 1 unit=120 μm.

The present invention provides improvements to the crystallization of iodixanol.

Thus viewed from one aspect the invention provides a process for the purification of a crude product comprising iodixanol by crystallization, wherein the crystallization involves wet milling.

The process according to the present invention reduces the process time for the crystallization steps and improves the washing and hence the purity of the final product.

DETAILED DESCRIPTION OF THE INVENTION

The processing time for the first crystallization is substantially longer than for the second one because of the higher concentration of impurities at this stage of the process. Due to the slow kinetics, both crystallizations are run at high initial supersaturation and during the crystallization process it is formed large agglomerates, often of more than 100 μm in diameter. These agglomerates are shown in FIG. 1. Agglomeration significantly reduces the available total surface area for crystal growth and therefore prolongs the process time to achieve the desired yield.

It has now surprisingly been found that it is possible to perform deagglomeration during the crystallization process by using wet milling.

Thus viewed from one aspect, the invention provides a process for the purification of a crude product comprising iodixanol by crystallization, wherein the crystallization solution is deagglomerated by wet milling.

The use of wet milling will significantly reduce the agglomeration of iodixanol crystals and by this reduce the process time for the crystallization steps. In cases where two crystallization steps are performed, the use of wet milling will be able to reduce the process time from about three days to less than two days for the first crystallization and from about two days to less than 1 day for the second crystallization.

Further, the use of wet milling in the crystallization step will also improve the purity of the final product. The purification process is finalized by filtering the precipitated iodixanol, preferably as unagglomerated crystals, from the solvents and finally washing the crystals with an alcohol such as methanol. The agglomerates of iodixanol crystals will also entrap mother liquor that needs to be removed by washing. By significantly reducing the agglomeration and hence the inclusion of mother liquor, a more effective washing of the crystals is achieved and also improved purity of the final product.

FIG. 1 shows agglomerates produced during a crystallization process according to prior art. It can be seen that the agglomerates have a mean size in the area of about 120 μm. FIG. 2 on the other hand shows particles produced under a process according to the present invention, and it can be seen that the particles are single crystals or very small agglomerates. The size of these particles is less then about 30 μm.

According to the present invention wet milling can be performed using any kind of mill, e.g. disc mills, colloid mills and other shear mixers.

Depending on the type of mill used, the mill can be mounted either into the crystallizer or in-line to the crystallizer. When mounted in-line to the crystallizer the crystallization solution is circulated between the crystallizer and the mill.

The mill can be used continuously throughout the crystallization, but normally a certain period at the start of the crystallization is sufficient to achieve the desired results.

The crude product referred to in the present invention can be obtained from the processes known from the state of the art, e.g. from the dimerisation process illustrated in Scheme I above. The dimerisation step itself may be carried out as described in European patent 108638 and WO 98/23296, for example using epichlorohydrin, 1,3-dichloro-2-hydroxypropane or 1,3-dibromo-2-hydroxypropane as the dimerisation agent, with epichlorohydrin being most preferred. The reaction is usually carried out in a solvent such as 2-methoxyethanol, methanol, 1-methoxy-2-propanol or a mixture of 2-methoxyethanol or 1-methoxy-2-propanol and water, and generally results in the conversion of 40 to 60% of Compound A to iodixanol.

Hence, in a second aspect of the invention it is provided a process for the manufacture of iodixanol comprising the steps of:
a) reacting 5-acetamido-N,N'-bis(2,3-dihydroxypropyl)-2,4,6-triiodo-isophthalamide with a dimerisation agent in the presence of a solvent
b) purifying the reaction product from step a) in a crystallization procedure
c) deagglomerating the crystallization solution in the crystallization procedure by wet milling
d) filtering and washing the product from step c)

The crude product from the dimerisation and following work-up steps is preferably in aqueous solution with small traces of organic solvent. The crude product normally contains about 75-90 weight % iodixanol, 3-10 weight % iohexyl, 0-7 weight % Compound A, and also minor amounts of other impurities. The most important impurities in the reaction with regard to work-up consequences are the so-called backpeaks. This term refers to retention times in reversed phase HPLC, where the backpeaks have slightly longer retention times than iodixanol itself. Most of the backpeaks are either trimers or O-alkylated dimers. This crude product is preferably the starting material for the further purification by crystallization according to the present invention.

The invention is illustrated further by the following examples that are not to be construed as limiting the invention in scope to the specific procedures or products described in them.

Example 1 shows a conventional crystallization process according to prior art without the use of wet milling. FIG. 1 shows agglomerates of iodixanol produced (1 unit=120 μm). The process reaches a yield of 80% after 54 hours. From the comparative example 2 showing the same process with the use of wet milling, it can be seen that a yield of 80% is reached as early as after 32 hours. In addition it can be seen that the purity of the final product is increased. FIG. 2 shows iodixanol particles produced (1 unit=30 μm).

In example 3 an optimized process with wet milling is described. Because of the shorter crystallization times involved, solvent can be added at an earlier stage than in a process according to prior art. In this process it can be seen that a yield of more than 80% is reached after only 23 hours.

Example 4 describes the process according to the present invention in a larger scale and with the use of a colloid mill. The crude product contained about 60% more backpeaks than in a comparable prior art process. However, by reducing the agglomeration by milling, the backpeak content after the first crystallization was similar to the backpeak content after the first crystallization in the prior art process. As for the prior art process, the product specification was met first after a further recrystallization not described in the example.

EXAMPLES

Example 1

305 g of crude product containing 253 g iodixanol, 17.8 g Compound A, 22.5 g iohexyl and 5.1 g backpeaks was dissolved in a mixture of water and 1-methoxy-2-propanol (PM) in a 1 liter vessel equipped with the a stirrer (with a magnet driven shaft), condenser and heating jacket. The amount of water and PM in the solution was 105 g and 442 g respectively. The solution was heated to reflux at atmospheric pressure and seeded with 2.4 g seed particles of iodixanol. Further addition of PM was done as follows:

| Start addition of PM (hrs after seeding) | Amount of PM (g) | Addition time (hrs) |
|---|---|---|
| 12 | 111 | 13 |
| 25 | 276 | 8 |

The yield of iodixanol was as follows:

| Time (hrs after seeding) | Yield of iodixanol (%) |
|---|---|
| 12 | 2 |
| 24 | 18 |
| 32 | 50 |
| 48 | 79 |
| 54 | 80 |

The product at the end of the crystallization was filtered and washed with methanol. The purity of the product is given below (HPLC):

| Substance | (%) |
|---|---|
| Iodixanol | 98.56 |
| Compound A | 0.10 |
| Iohexol | 0.21 |
| Backpeaks | 1.07 |

FIG. 1 shows iodixanol agglomerates produced.

Example 2

305 g of crude product containing 253 g iodixanol, 17.8 g Compound A, 22.5 g iohexyl and 5.1 g backpeaks was dissolved in a mixture of water and 1-methoxy-2-propanol (PM) in a 1 liter vessel equipped with the a stirrer (with a magnet driven shaft), disc mill, condenser and heating jacket. The amount of water and PM in the solution was 105 g and 442 g respectively. The solution was heated to reflux at atmospheric pressure and seeded with 2.4 g seed particles of iodixanol. Further addition of PM was done as follows:

| Start addition of PM (hrs after seeding) | Amount of PM (g) | Addition time (hrs) |
|---|---|---|
| 12 | 111 | 13 |
| 25 | 276 | 8 |

The yield of iodixanol was as follows:

| Time (hrs after seeding) | Yield of iodixanol (%) |
|---|---|
| 12 | 57 |
| 24 | 71 |
| 32 | 80 |

-continued

| Time (hrs after seeding) | Yield of iodixanol (%) |
| --- | --- |
| 48 | 83 |
| 54 | 83 |

The product at the end of the crystallization was filtered and washed with methanol. The purity of the product is given below (HPLC):

| Substance | (%) |
| --- | --- |
| Iodixanol | 99.00 |
| Compound A | 0.05 |
| Iohexol | 0.05 |
| Backpeaks | 0.86 |

FIG. 2 shows iodixanol particles produced.

Example 3

305 g of crude product containing 253 g iodixanol, 17.8 g Compound A, 22.5 g iohexyl and 5.1 g backpeaks was dissolved in a mixture of water and 1-methoxy-2-propanol (PM) in a 1 liter vessel equipped with the a stirrer (with a magnet driven shaft), disc mill, condenser and heating jacket. The amount of water and PM in the solution was 105 g and 442 g respectively. The solution was heated to reflux at atmospheric pressure and seeded with 2.4 g seed particles of iodixanol. Further addition of PM was done as follows:

| Start addition of PM (hrs after seeding) | Amount of PM (g) | Addition time (hrs) |
| --- | --- | --- |
| 10 | 111 | 4 |
| 14 | 276 | 4 |

The yield of iodixanol was as follows:

| Time (hrs after seeding) | Yield of iodixanol (%) |
| --- | --- |
| 10 | 51 |
| 14 | 65 |
| 18 | 78 |
| 23 | 81 |
| 35 | 82 |

The product at the end of the crystallization was filtered and washed with methanol. The purity of the product is given below (HPLC):

| Substance | (%) |
| --- | --- |
| Iodixanol | 99.0 |
| Compound A | 0.05 |
| Iohexol | 0.05 |
| Backpeaks | 0.86 |

Example 4

An aqueous solution of crude iodixanol product was concentrated in a vessel and 1-methoxy-2-propanol (PM) was added. The content of water was then adjusted to the desired level. The solution contained about 60 kg iodixanol, 4 kg Compound A, 4 kg iohexyl and 2 kg backpeaks. The vessel was equipped with a stirrer, condenser, colloid mill (MK2000/4 from IKA™) in loop to the vessel and heating jacket. The crude product contained about 60% more backpeaks than in a comparable prior art process. The amount of water and PM in the solution was 19 kg and 58 kg respectively. The solution was heated to reflux at atmospheric pressure and seeded with 0.56 kg seed particles of iodixanol. Further addition of PM was done as given in the table below. The water content was reduced by 14% by distillation during the crystallization.

| Start addition of PM (hrs after seeding) | Amount of PM (kg) | Addition time (hrs) |
| --- | --- | --- |
| 10 | 19 | 6 |
| 16 | 38 | 6 |

The yield of iodixanol was as follows:

| Time (hrs after seeding) | Yield of Iodixanol (%) |
| --- | --- |
| 11 | 61 |
| 14 | 68 |
| 37 | 88 |

The product at the end of the crystallization was filtered and washed with methanol. The purity of the product is given below (HPLC):

| Substance | (%) |
| --- | --- |
| Iodixanol | 98.7 |
| Compound A | 0.07 |
| Iohexol | 0.04 |
| Backpeaks | 1.09 |

The iodixanol particles produced using the mill during for the first 11 hours of a total crystallization time of 37 hours, are shown in FIGS. 3A and 3B. FIG. 3A shows the particles 13 hours after seeding and the FIG. 3B shows the particles 37 hours after seeding.

All patents, journal articles, publications and other documents discussed and/or cited above are hereby incorporated by reference.

I claim:

1. An improved process for the purification of a crude reaction mixture resulting from the dimerisation of Compound A comprising iodixanol, Compound A, iohexol and backpeaks comprising the step of wet milling said crude reaction mixture during the crystallization process of said crude reaction mixture.

* * * * *